United States Patent [19]
Hedges

[11] Patent Number: 5,520,659
[45] Date of Patent: May 28, 1996

[54] SYRINGE NEEDLE COVER AND VIAL CONNECTOR

[75] Inventor: Harry S. Hedges, Kalamazoo, Mich.

[73] Assignee: Joseph K. Andonian, Portage, Mich.

[21] Appl. No.: 208,142

[22] Filed: Mar. 9, 1994

[51] Int. Cl.$^6$ .................................................. A61M 5/32
[52] U.S. Cl. ........................ 604/192; 604/187; 604/905; 604/414
[58] Field of Search ..................... 604/192, 414, 604/187, 403, 411, 415, 197, 200, 201, 110, 905, 283; 128/764, 770, 919; 141/329, 330, 368, 369, 370, 372, 384

[56] References Cited

U.S. PATENT DOCUMENTS

| | | | |
|---|---|---|---|
| 2,845,068 | 7/1958 | Gabriel | 604/414 |
| 3,826,260 | 7/1974 | Killinger . | |
| 3,826,261 | 7/1974 | Killinger . | |
| 4,475,915 | 10/1984 | Sloane | 604/414 |
| 5,240,047 | 8/1993 | Hedges | 141/21 |
| 5,247,972 | 9/1993 | Tetreault | 141/27 |
| 5,322,515 | 6/1994 | Karas et al. | 604/192 |

FOREIGN PATENT DOCUMENTS

PCT/US90/
03481 10/1991 WIPO .

OTHER PUBLICATIONS

Webster's New World Dictionary, 3rd Editon, p. 1278 (1988).

Primary Examiner—C. Fred Rosenbaum
Assistant Examiner—V. Alexander
Attorney, Agent, or Firm—Joseph K. Andonian

[57] ABSTRACT

The combination of a syringe and needle cover that not only provides protection for the needle prior to use of the syringe but also facilitates the mating the syringe to a vial without exposing the needle to the user until the syringe is filled and ready for injection. Advantages include greater economy, convenience, simplicity and safety than prior art devices.

6 Claims, 5 Drawing Sheets

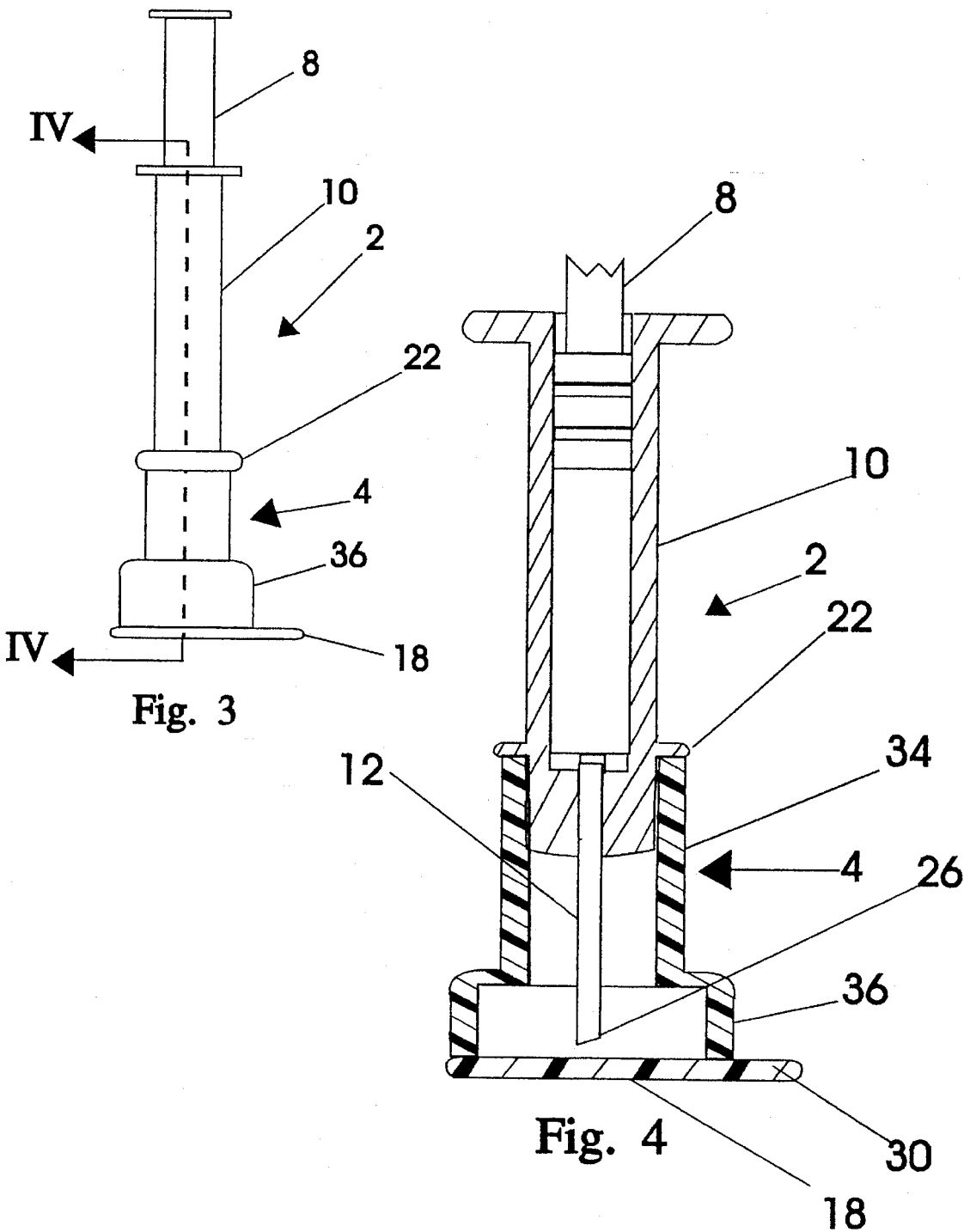

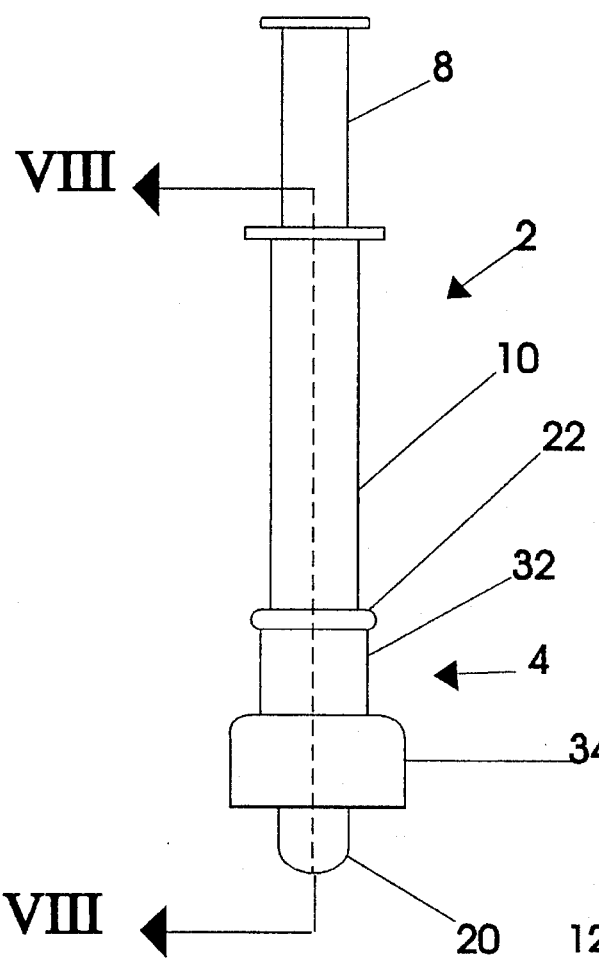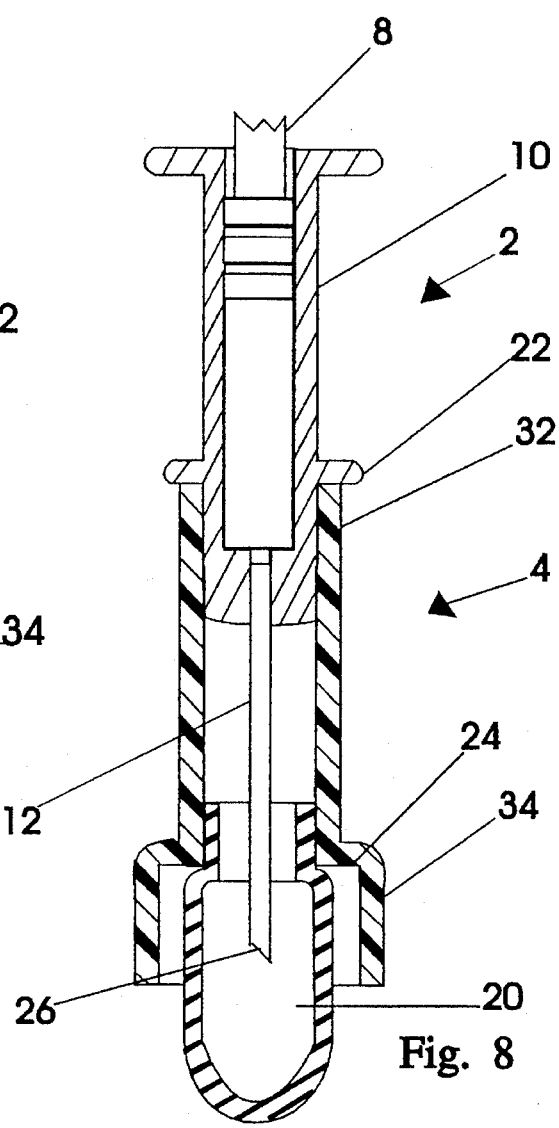

SYRINGE NEEDLE COVER AND VIAL CONNECTOR

BACKGROUND OF THE INVENTION

This invention relates primarily to a syringe and needle cover combination that can more safely and conveniently be combined with a vial containing a medicament for the purpose of filling the syringe.

Prior art syringe needles are usually covered with a simple cap that is capable only of protecting the needle. To fill the syringe with medicament, the cap is simply removed by hand and the needle fitted manually into the stopper of a vial for the purpose of filling the syringe with medicament. To fit the needle safely and conveniently into the bull's eye on the stopper on the top of a vial, many devices are already available in the prior art, including the syringe guide of the present inventor described in U.S. Pat. No. 5,240,047. However, these prior art devices are more complex and expensive to produce than the present device. They even require more dexterity from and incur more risk of injury to the user of the syringe. The user must uncover the needle and insert it into a passageway of some kind in order to guide the needle to the bull's eye, penetrate the stopper with the needle and fill the syringe. Although such guides were improvements over their predecessors, an exposed needle still requires considerable dexterity and visual acuity to find a passageway and penetrate the vial. Further reduction in the risk of injury or complexity is still desirable especially for the visually or physically impaired, inexperienced or distracted user of a syringe particularly since accidental puncture of the skin with a needle can result in transmittal of virus-infected blood. A need therefore exists for a more convenient, simple, economical and safe device for filling a syringe.

OBJECTS AND SUMMARY OF THE INVENTION

The principal object of the present invention is to satisfy the need for a more convenient, simple, economical and safe device to provide a protective cover for a syringe needle and facilitate the filling of a syringe from a vial containing a liquid medication.

The principal feature of the present invention is the provision of a device that serves initially as a protective cover for a syringe needle and thence insures that the needle or cannula of the syringe can be inserted into a vial in a safe and easy manner for maximum drug and minimal air extraction from the vial without risk of injury to the user of the syringe.

Another feature of the present invention is the tubular sheath structure that allows it to be carried separately for mating to a syringe that already possesses a needle cover to facilitate mating the syringe to a vial after the needle cover is removed.

Still another feature of the present invention is to allow the user to have an unobstructed view of the contents of the vial, the markings on the syringe and the location of the needle in the vial to assure proper filling of the syringe.

In addition the present invention is especially advantageous for use by the elderly, the physically impaired, the inexperienced, those required to act quickly and even those who have only one hand available for filling a syringe.

The principal component of the present invention is a tubular sheath in which (1) one portion is adapted to securely yet removably receive the needle end of a syringe, (2) the opposite portion of the sheath is adapted to securely yet removably receive the needle-penetrable stopper on a vial and (3) the intervening tunnel or passage is adapted to enclose the needle and enable the sheath to extend just beyond the tip of the needle after attachment to a syringe. One stop, preferably in the form of an annular ring, is preferably positioned on the outside of the syringe barrel and a second stop is preferably positioned on the inside of the vial end of the sheath. Together the two stops are positioned just far enough apart to allow the syringe and the vial cap to fit inside the sheath to securely but removably mate the syringe and vial to the sheath and at the same time permit the needle to penetrate just past the inside surface of the vial stopper.

In the most preferred embodiment of the present invention the above-described tubular sheath is attached to the needle end of a syringe and the opposite end of the sheath is covered with a removable seal. An adhesive seal, like those used inside the cap of many food products, is suitable for this purpose. Thus the sealed sheath functions as a needle cap and preserves the sterility and physical integrity of the needle prior to use. Once the seal is removed the sheath is ready for attachment to a vial allowing the uncovered needle to penetrate the stopper in the vial for the purpose of filling the syringe.

In another embodiment of the present invention the tubular sheath is attached to the needle end of a syringe and a cap is fitted over the end of the needle into the narrower passageway inside the sheath. The cap is firmly but removably fitted inside the sheath and is long enough to enable the user to grip the cap between his or her fingers. The combination of the sheath and the cap completely encloses the needle to maintain its sterility and physical integrity until the cap is removed prior to attachment of the sheath to a vial for filling the syringe.

After filling the syringe following use of the foregoing embodiments of the invention, the sheath and vial are preferably separated from the syringe as a unit. The syringe is then ready for use and subsequent disposal in the usual manner. Similarly the sheath can be separated from the vial and discarded or reused.

The invention will be better understood and further objects and advantages thereof will become more apparent from the ensuing detailed description taken in conjunction with the drawings.

BRIEF DESCRIPTION OF THE DRAWINGS

FIG. 3 is a side elevational view of the tubular sheath 4 attached to a syringe 2 with a adhesive seal 18 on the unattached end;

FIG. 4 is a cross-sectional view taken along the line IV—IV of FIG. 3;

FIG. 7 is a side elevational view of the tubular sheath 4 attached to a syringe 2 with a needle cap 20; and FIG. 8 is a cross-sectional view taken along line VIII—VIII of FIG. 7.

Figure 1:
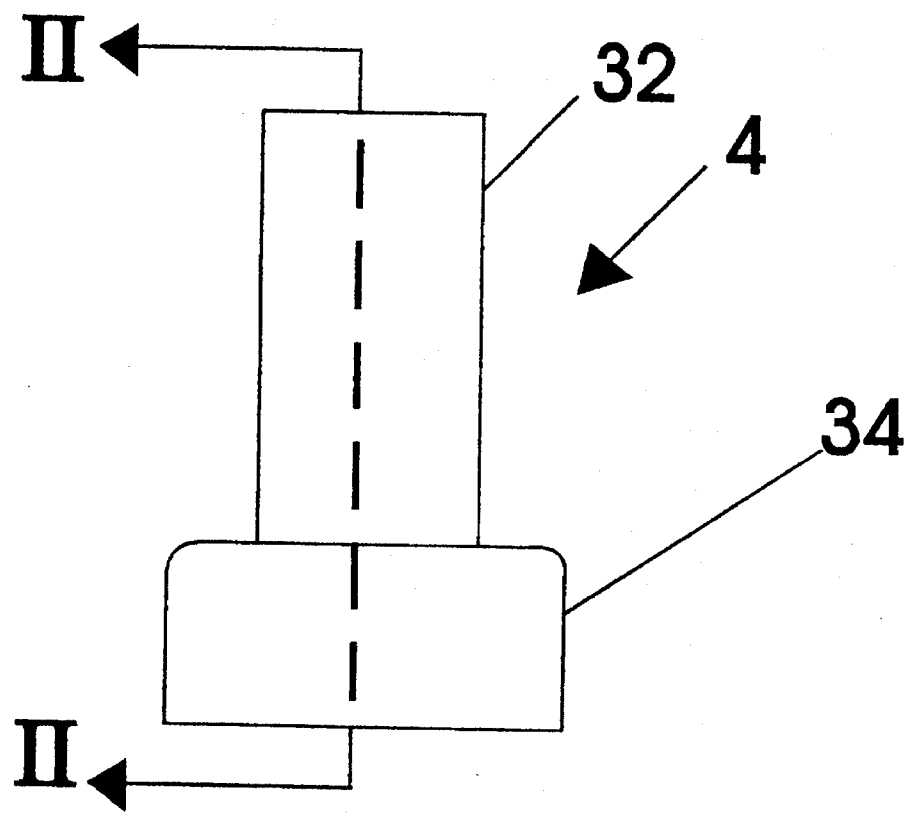
FIG. 1 is a side elevational view of the tubular sheath 4.

The figures are not drawn to exact scale.

Reference numerals in drawings

2 Syringe
4 Tubular sheath
6 Vial
8 Syringe plunger
10 Syringe barrel
12 Needle
14 Vial stopper
16 Metal cap on vial
18 Adhesive type seal
20 Needle cap
22 Stop on syringe
24 Vial stop on inside of tubular sheath
26 Tip of needle
30 Pull tab for adhesive type seal
32 Syringe holding portion of the tubular sheath
34 Vial holding portion of the tubular sheath
38 Plug type seal
40 Cap type seal

DETAILED DESCRIPTION

Figure 2:
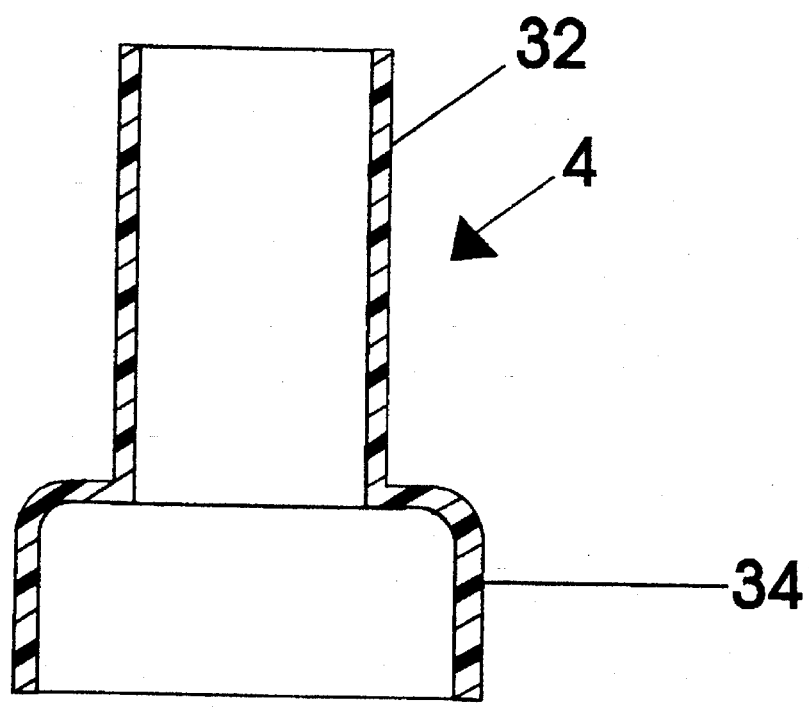
FIG. 2 is a cross-sectional view taken along the line II—II of FIG. 1.
Figure 5:
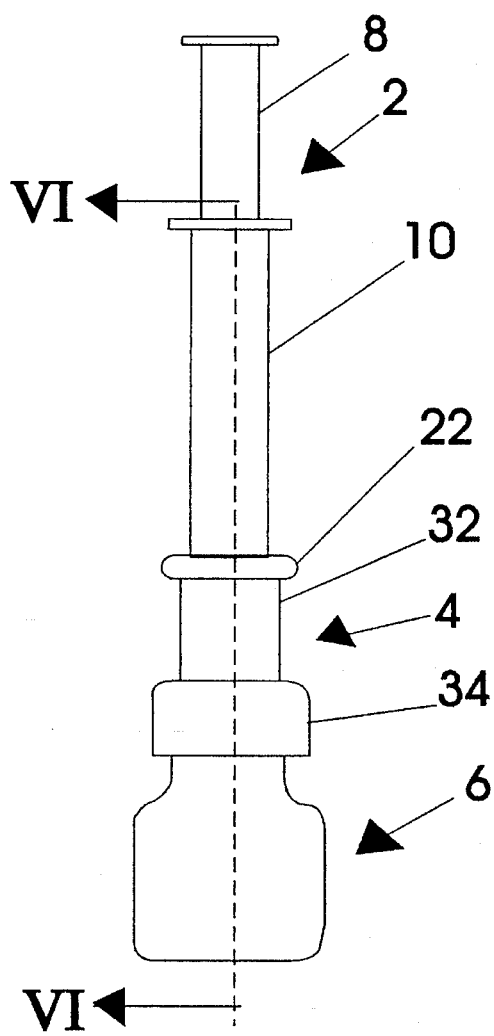
FIG. 5 is a side elevational view of the tubular sheath 4 device attached to a syringe 2 and vial 6.
Figure 6:
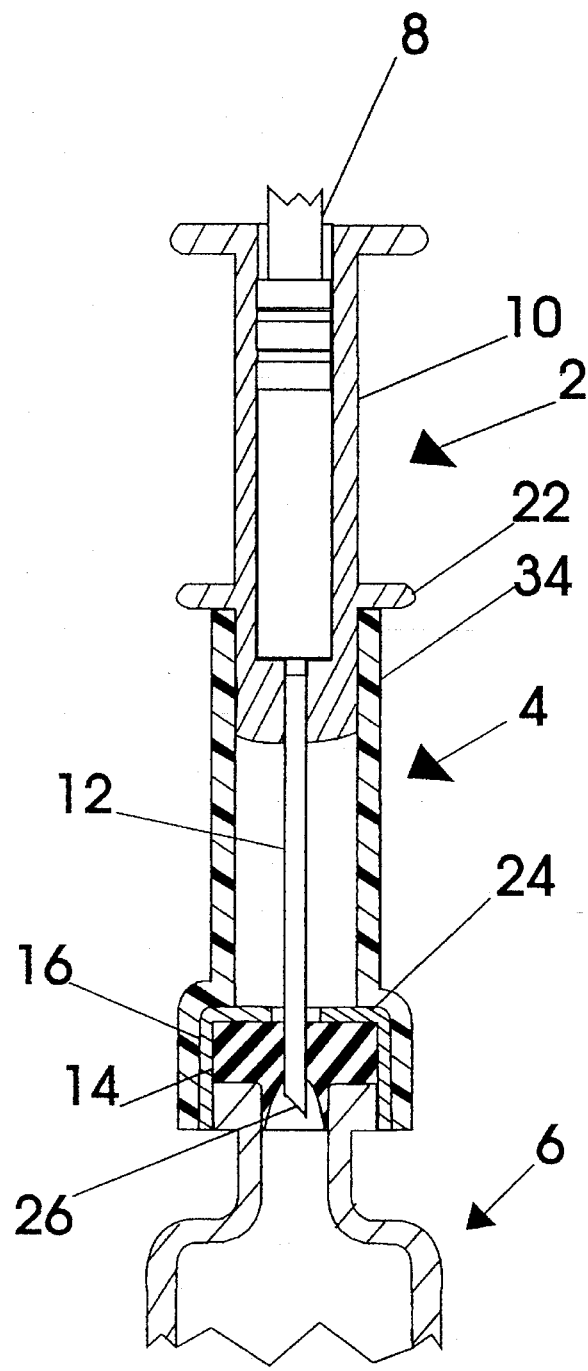
FIG. 6 is cross-sectional view taken along the line VI—VI of FIG. 5.
Figure 9A:
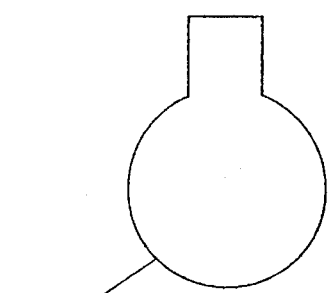
FIG. 9 provides two views of each, of the three types of seal—18, 38, 40—that can be used on the vial end 34 of the sheath 4.
Figure 9B:
Figure 9C:
Figure 9D:
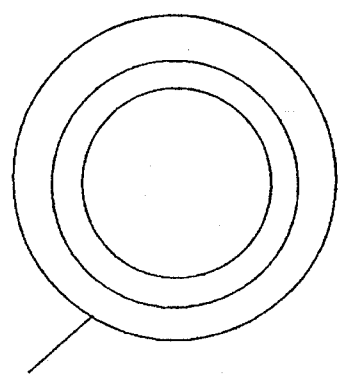
Figure 9E:
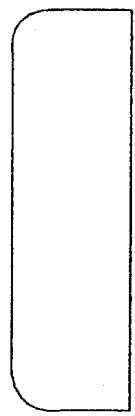
Figure 9F:
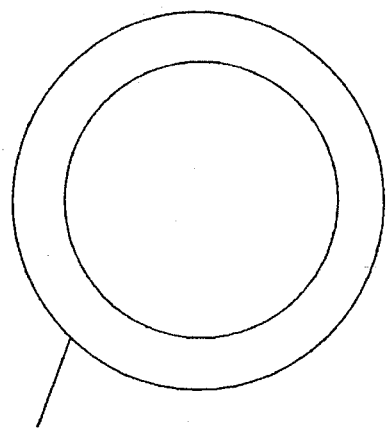

FIGS. 1 and 2 depict the tubular sheath 4 in elevational and cross-sectional presentations of the principal component of the present invention. It could be useful as a separate and distinct product to users of a syringe for repeated use only if a syringe were fitted with a cap that covers the needle and includes a structural modification not depicted in the drawings that would permit sheath 4 to fit over the needle cover onto the barrel of the syringe. The needle cap would then have to be removable without removing the sheath 4.' The sheath per se is more useful to manufacturers to use as a component of assemblies such as depicted in FIGS. 3 and 7, FIGS. 3 and 4 depict the combination of syringe 2, tubular sheath 4 and adhesive seal 18. A plug 38 or a cap 40 could also be substituted to seal the vial end 34 of sheath 4. In this embodiment of the invention the adhesive seal 18 must be removed before attaching the tubular sheath 4 to the vim 6 as depicted in FIGS. 5 and 6. The vial and syringe holding portions 32 and 34 of the tubular sheath 4 generally consist of a cylindrical shape conforming to the cylindrical shape of conventional syringes and vials such as 2 and 6. Other shapes are also possible as long as the contact surfaces of the syringe 2, tubular sheath 4 and vial 6 can form a firm but removable attachment to each other as depicted. The external shape of the tubular sheath 4 is even less critical to the present invention. A degree of elasticity in the tubular sheath 4 would allow the tubular sheath 4 to be slightly expanded to provide a suitable friction-fit when attached to syringe 2 and vial 6. The tubular sheath 4 can be formed of a suitable material, such as either opaque or semitransparent plastic preferably possessing a degree of elasticity.

FIG. 5, depicts a syringe 2 attached to a vial 6 by the tubular sheath 4 of the present invention. FIG. 6 depicts the same combination in somewhat enlarged cross section revealing the needle 12 penetrating through the vial stopper 14. The tip of the needle 26 is positioned so that it is capable of extracting the entire contents of the vial 6 when the vial 6 is tipped up to extract the contents from the vial 6 into the syringe. FIG. 6 also reveals the metal cap 16 which helps to hold the stopper 14 firmly in place inside the neck of vial 6. The metal cap 16 also has an opening which forms a bull's eye at the center of the stopper 14. When the tubular sheath 4 is fitted onto the vial 6 it's configuration assures that the needle 12 will contact and penetrate the vial stopper at the bull's eye. FIG. 6 also illustrates the proper length of the tubular sheath, namely sufficient to enclose the needle prior to use and allow the needle during use to penetrate the stopper 14 to the proper depth and yet provide a firm but removable grip on the syringe 2 and the vial 6. The inside configuration of the ends of the sheath 4 are designed to provide a friction fit on the syringe 2 at one end and the top of the vial 6 at the other end. The stops 22 and 24 are positioned to provide sufficient depth to accomplish the desired grip on the syringe 2 and vial 6. Instead of providing stops as depicted, one stop could be provided on the inside of the sheath 4 for attachment over the barrel 10 of the syringe 2 and another stop could be provided on the neck of the vial 6. The essential feature is that both the syringe 2 and the vial 6 are firmly but removably fitted into the ends of sheath 4 and the sheath 4 provides sufficient additional length to extend past the tip 26 of the needle 12 when attached to the syringe 2. The stop 22 depicted on the syringe barrel 10 is preferred primarily because syringes possessing that structure are already available commercially albeit the stop is intended for use to butt up against the open end of a conventional cap to enclose and protect the needle. One end of a conventional cap is closed and obviously cannot be used to mate with a vial like the product of the present invention.

A different embodiment of the invention is depicted in FIGS. 7 and 8. Syringe 2 is affixed to sheath 4 with a needle cap 20 fitted on the inside of the passage between the syringe holding 32 and vial holding 34 portions of sheath 4 over the tip 26 of needle 12 as most clearly shown in FIG. 8.

FIG. 9 depicts the three types of seals—18, 38 and 40—that can be used alternatively in an assembly such as depicted in FIG. 3.

The preferred commercial embodiment of the present invention is depicted in FIGS. 3 and 4. A somewhat less preferred embodiment of the present invention is depicted in FIGS. 7 and 8. The embodiment depicted in FIGS. 1 and 2 is most useful as a component for manufacturers of syringes to use to complete such assemblies as illustrated in FIGS. 3 and 7. The principal advantage envisioned for this last embodiment if sold to and used by consumers is the economy of using the sheath 4 several times with syringes especially designed for use with sheath 4. In this embodiment the user also has the option of using a syringe without using the sheath on those occasions when the sheath seems unnecessary. In all three depicted and described embodiments the present device can be used more economically and easily with much less risk of accidentally puncturing and possibly infecting the user or the patient. While the ease of use is most important for inexperienced or physically and visually impaired users, even those not so impaired are sometimes distracted, tired or hurried and would thereby benefit from use of the present invention.

The operation of the version of the invention depicted in FIGS. 3 and 4 is simple. The user merely removes the seal 18, draws the proper amount of air into the syringe, fits the top of the vial 6 into the open end of the tubular sheath 4 until the vial 6 is firmly seated and fills the syringe 2 in the conventional manner, namely by injecting the air from the syringe 2 into the vial with the tip 26 pointed down and then reversing the tip 26 up and filling the syringe 2. The vial 6 which still attached to sheath 4 is separated from syringe 2 which is then ready for injection. The vial 6 can be separated from sheath 4 separately.

The operation of the version of the invention depicted in FIGS. 7 and 8 differs only in removal of the needle cap 20 before attachment to the vial 6 and extraction of the medicinal liquid from the vial 6 into the syringe 2.

The operation of the version depicted in FIGS. 1 and 2 differs in the requirement of attachment of the sheath 4 preferably by the manufacturer to the syringe 2, and thence following the foregoing steps for whatever embodiment of the invention is manufactured.

The foregoing relates essentially to preferred exemplary embodiments of the present invention, it being understood that other embodiments and variants thereof are possible within the scope of the invention as defined by the legal scope of the appended claims.

What is claimed is:

1. The combination consisting essentially of a syringe having a barrel with a needle affixed to one end of the said syringe barrel wherein said needle extends outward from said syringe barrel and terminates in a tip suitable for injection, a two-ended tubular sheath friction fitted at its first end completely around the said needle end of said syringe, and removable seal means affixed to the second end of the said sheath wherein the said second end of the said sheath has internal configuration means capable of providing a friction fit completely around the top of a medicinal vial having a needle penetrable stopper on the top said vial, wherein the said second end of said sheath extends a short distance beyond the tip of the said needle when said first end of said sheath is attached to said syringe and together with the said seal completely encloses the said needle within the said sealed sheath, and wherein the said sheath has an internal bore large enough in diameter to enclose said needle and long enough to enable the said tip of the said needle, after removal of the said seal, to penetrate just inside the stopper of the said vial when said vial is connected to the said second end of the said sheath and thereby facilitate the substantially complete evacuation of the contents of the said vial.

2. The combination of claim 1 wherein the first end of the said sheath butts up against a stop on the barrel of the said syringe and the second end of said sheath possesses a stop on its inside surface capable of butting up against the top of the said vial.

3. The combination of claim 1 wherein the sheath is composed of an elastic material.

4. A device suitable for (a) covering a needle extending outwardly from and affixed to one end of the barrel of a syringe wherein said needle extends outward from said syringe barrel and terminates in a tip suitable for injection and (b) connecting the said syringe to the top of a vial having a needle penetrable stopper which seals the top of said vial, said devices consisting essentially of a tubular sheath having a first end with internal bore means adapted to fit firmly but removably over the needle end of said syringe, having a second end with internal bore means adapted to fit firmly but removably over the stoppered end of said medicinal vial, having an intermediate passage between the first and second ends of said sheath with an internal configuration large enough in diameter to enclose said needle and long enough to permit said sheath to extend just beyond the tip of said needle when said sheath is attached to said syringe, and having removable sealing means on the second end of said sheath capable of fully enclosing said needle in combination with said sheath and said syringe prior to attachment of said vial to said sheath.

5. The device of claim 4 wherein the length of said sheath is adjusted to enable said needle to penetrate just inside the stopper of said vial to permit the substantially complete evacuation of the said vial when said sealing means is removed and the said sheath is connected to said syringe and said vial.

6. The device of claim 4 wherein the said sheath is composed of an elastic plastic material.

* * * * *